Dec. 30, 1958 H. ROBINSON Plant Pat. 1,790
ROSE PLANT
Filed May 19, 1958
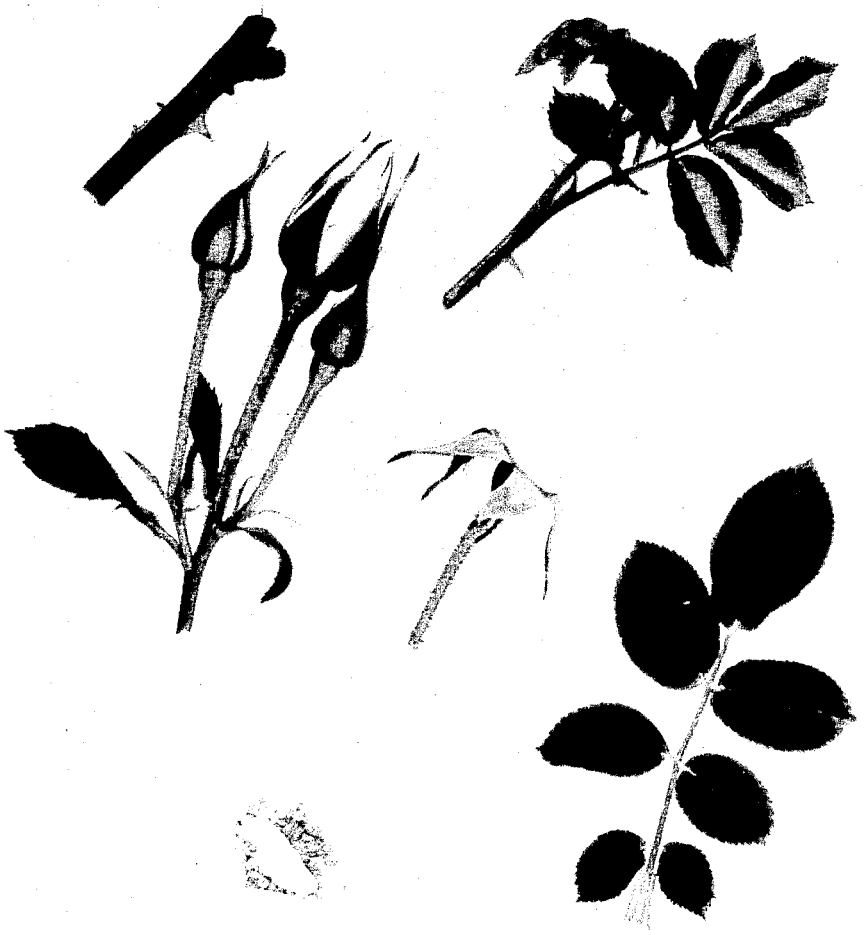
Inventor
Herbert Robinson
By: Robb & Robb
Attorneys United States Patent Office Plant Pat. 1,790
Patented Dec. 30, 1958

1,790

ROSE PLANT

Herbert Robinson, Burbage, Hinckley, England, assignor to Jackson & Perkins Company, Newark, N. Y., a corporation of New York Application May 19, 1958, Serial No. 736,416

1 Claim. (Cl. 47—61)

The present invention relates to a new and distinct variety of rose plant of the large-flowered hybrid floribunda class, which was originated by me by crossing the variety "Pinocchio" (U. S. Plant Patent No. 484) with the variety "Peace" (U. S. Plant Patent No. 591).

The primary objective of this breeding was to produce a new rose variety which combines some of the growth characteristics and size of the parent variety "Peace" with the blooming qualities of the parent variety "Pinocchio." This objective was fully achieved, along with other improvements, as evidenced by the following unique combination of characteristics which are outstanding in the new variety:

(1) A vigorous, tall-growing and bushy plant;

(2) A floriferousness which is greater than that of the variety "Pinocchio" and which continues throughout the entire growing season;

(3) Long shoots which are unusual in such a floriferous variety;

(4) Long-lasting quality of the flower petals, generally similar to the long-lasting quality of "Peace"; and (5) A distinctive Massicot Yellow, lightly overcast with Buff-Yellow general color tonality of the flowers.

The foregoing characteristics and distinctions definitely differentiate my new variety from its parents, as well as from all other varieties of which I am aware, and asexual reproduction of the new variety by budding, as performed at Newark, New York, U. S. A. and also at Pleasanton, California, U. S. A., shows that the aforesaid characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Pinocchio."
*Pollen parent.*—"Peace."
Classification:
*Botanic.*—Large-flowered hybrid floribunda.
*Commercial.*—Grandiflora.

*Flower*

(Observations made from specimens grown outdoors at Newark, New York, U. S. A. in the early afternoon near the middle of September.)

Blooming habit: Recurrent—continuous.
Bud:
*Size.*—Medium.
*Form.*—Ovoid; is not affected by wet or hot weather.
*Color.*—When sepals first divide—Picric Yellow, Plate 4. When petals begin to unfurl—Empire Yellow, Plate 4. When half-blown: inside of petals—Buff-Yellow, Plate 4, with outer edge of petal lightly overcast with Straw Yellow, Plate 16; reverse of petals—Massicot Yellow, Plate 16, lightly overcast with Mustard Yellow, Plate 16.
*Sepals.*—Serrated; slightly branched; curl back when petals begin to unfurl. Color: inside—Kildare Green, Plate 31; outside—Cress Green, Plate 31.
*Calyx.*—Color—Cress Green, Plate 31. Shape—pear. Size—small. Aspect—smooth. Odor when rubbed—none.
*Peduncle.*—Length — medium. Aspect — prickly. Strength—erect; slender. Color—Rainette Green, Plate 31.
*Opening.*—Opens up well; is not affected by adverse weather conditions.

Bloom:
*Size.*—Large. Average size when fully expanded—4½ inches.
*Borne.*—Several together and in irregular clusters.
*Stems.*—Long; strong.
*Form (when first open).*—Cupped. Permanence—like a show Dahlia.
*Petalage.*—Double (full but open center). Number of petals under normal conditions—from 25 to 30.
*Color.*—Center of flower—Buff-Yellow, Plate 4. Outer petals—Marguerite Yellow, Plate 30, with lower half of petal lightly overcast with Maize Yellow, Plate 4. Base of petals (aiglet)—Empire Yellow, Plate 4. Inside of petals—Massicot Yellow, Plate 16, with lower half of petal lightly overcast with Buff-Yellow, Plate 4. Reverse of petals—Sea-Foam Yellow, Plate 31, with lower half of petal lightly overcast with Buff-Yellow, Plate 4. General tonality from a distance—Massicot Yellow, Plate 16, lightly overcast with Buff-Yellow, Plate 4.
*Discoloration.*—General tonality at end of first day—Massicot Yellow, Plate 16. Second day—Massicot Yellow, Plate 16, lightly overcast with Buff-Yellow, Plate 4. Third day—Marguerite Yellow, Plate 30, lightly overcast with Maize Yellow, Plate 4.

Petals:
*Texture.*—Leathery; is not affected by wet or hot weather.
*Appearance.*—Inside—satiny. Outside—shiny.
*Form.*—Oval.
*Arrangement.*—Informal (with "rags" in center).
*Petaloids incenter.*—Few; large.
*Persistence.*—Drop off cleanly.
*Fragrance.*—Moderate. Nature—tea (average hybrid tea scent).
*Lasting quality.*—On the plant—long. As cut flower—very long.

*Genital organs*

Stamens, anthers: Large; many; regularly arranged around styles. Color—Cadmium Orange, Plate 3.
Stamens, filaments (threads): Long. Color—Capucine Buff, Plate 3.
Pollen: Color—Pale Yellow-Orange, Plate 3.
Styles: Loosely separated; uneven length; medium length; thin.
Stigmas: Color—Antimony Yellow, Plate 15.
Ovaries: All enclosed in calyx.
Hips: None.
Seeds: None.

*Plant*

Form: Bush.
Growth: Vigorous; upright; bushy.

Foliage: Compound of 5 to 7 leaflets.

*Size.*—Medium.

*Quantity.*—Normal.

*Color.*—New foliage: upper side—Chromium Green, Plate 32, with serrations of Oxblood Red, Plate 1; under side—Courge Green, Plate 17, lightly overcast with Van Dyke Red, Plate 13. Old foliage: upper side—Dark Cress Green, Plate 31; under side—Light Cress Green, Plate 31.

*Shape.*—Oval.

*Texture.*—Upper side — leathery; glossy. Under side—smooth.

*Ribs and veins.*—Ordinary.

*Edge.*—Serrated (saw-toothed).

*Serration.*—Both double and single; small.

*Leaf stem.*—Color—Light Elm Green, Plate 17. Under side—smooth.

*Stipules.*—Medium length; serrated.

Wood:

*New wood.*—Color—Light Bice Green, Plate 17. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form— narrow base; medium length; straight. Color (when young)—Acajou Red, Plate 13. Position—irregular.

*Prickles.*—Quantity: on main stalks from base—none; on laterals from stalk—none.

*Short needles.*—Quantity: on main stalks from base—none; on laterals from stalk—none.

I claim:

A new and distinct variety of rose plant of the large-flowered hybrid floribunda class, substantially as herein shown and described, characterized particularly as to novelty by the unique combination of vigorous, tall and bushy plant growth, a floriferousness greater than that of the parent variety "Pinocchio" (U. S. Plant Patent No. 484) and the continuation thereof throughout the entire growing season, unusually long shoots, long-lasting petal quality similar to that of the parent variety "Peace" (U. S. Plant Patent No. 591), and a distinctive Massicot Yellow, lightly overcast with Buff-Yellow general color tonality of the flowers.

No references cited.